(12) United States Patent
Aygen

(10) Patent No.: US 7,037,487 B2
(45) Date of Patent: May 2, 2006

(54) METHOD FOR DIAGNOSING LACTOSE INTOLERANCE AND DIAGNOSTIC KIT FOR PERFORMING THE METHOD

(76) Inventor: Sitke Aygen, Gottfried-Hagen-Str. 60-62, Köln (DE) 51105

( * ) Notice: Subject to any disclaimer, the term of this patent is extended or adjusted under 35 U.S.C. 154(b) by 314 days.

(21) Appl. No.: 10/380,466

(22) PCT Filed: Sep. 18, 2001

(86) PCT No.: PCT/EP01/10767

§ 371 (c)(1),
(2), (4) Date: Mar. 19, 2003

(87) PCT Pub. No.: WO02/27325

PCT Pub. Date: Apr. 4, 2002

(65) Prior Publication Data

US 2004/0087837 A1    May 6, 2004

(30) Foreign Application Priority Data

Sep. 27, 2000  (DE)  ................................ 100 60 989

(51) Int. Cl.
*A61K 51/00*  (2006.01)
*A61M 36/14*  (2006.01)

(52) U.S. Cl. .................. 424/1.81; 424/1.11; 424/1.65; 424/9.1; 424/9.2; 424/1.73

(58) Field of Classification Search ............... 424/1.11, 424/1.37, 1.65, 1.81, 9.1, 9.2, 1.73; 206/223, 206/569, 570

See application file for complete search history.

(56) References Cited

U.S. PATENT DOCUMENTS 5,640,014 A    6/1997   Sauke et al.

OTHER PUBLICATIONS

Peuhkuri et al., "Wide variations of the testing of lactose tolerance: results of a questionnaire study in Finnish health care centres", XP-001027414, *Scandinavian Journal of Clinical and Laboratory Investigation*, vol. 60, No. 4, (Jul. 2000), p. 291-298.

Hiele et al., " Carbon-13 Dioxide Breath Test Using Naturally Carbon-13-Enriched Lactose for Detection of Lactase Deficiency in Patients with Gastrointestinal Symptoms", XP-00102178, *Journal of Laboratory and Clinical Medicine*, vol. 112, No. 2, (1988), pp. 193-200.

Murray et al., "Comparative Absorption of Carbon-13 Glucose and Carbon-13 Lactose by Premature Infants", XP-001027415, *American Journal of clinical Nutrition*, vol. 51, No. 1, (1990), pp. 59-66.

Hermans et al., "The Relationship Between Lactose Tolerance Test Results and symptoms of Lactose Intolerance", XP-001027136, *American Journal of Gastroenterology*, vol. 92, No. 6, (1997), pp. 981-984.

Vonk Roel et al., "Small Intestinal and Colonic Factors Involved in Lactose Intolerance", XP-001027262, *FASEB Journal*, vol. 15, No. 4, (Mar. 2001), pp. p. A277, Annual Meeting of the Federation of American Societies for Experimental Biology on Experimental Biology 2001.

Vonk et al., The 13C/2H-Glucose Test For Determination of Small Intestinal Lactase Activity, XP-000998471, *European Journal of Clinical Investigations*, vol. 31, No. 3, (2001), pp. 226-233.

Primary Examiner—Dameron L. Jones
(74) Attorney, Agent, or Firm—Jacobson Holman PLLC

(57) ABSTRACT

The method for diagnosing lactose intolerance in patients by the oral administration of defined amounts of lactose, followed by assaying metabolites of lactose, is performed in a way where the lactose administered contains 99% $^{13}$C-labeled lactose, preferably from 5 to 30 mg, and after the administration of the lactose, the content of $^{13}$C-labeled lactose is determined in a serum sample taken at a defined time after the administration. A diagnostic kit for performing the method consists of a capsule with from 5 to 30 mg of 99% $^{13}$C-labeled lactose, a patient instruction manual, a blood sampling device, sample containers for collecting the blood sample, and optionally a spatula and sample container for a stool specimen.

7 Claims, No Drawings

METHOD FOR DIAGNOSING LACTOSE INTOLERANCE AND DIAGNOSTIC KIT FOR PERFORMING THE METHOD

This is a nationalization of PCT/EP01/10767 filed Sep. 18, 2001 and published in German.

The present invention relates to a method for diagnosing lactose intolerance in patients by the oral administration of defined amounts of lactose, followed by assaying metabolites of lactose, and a diagnostic kit for performing the method.

Lactose intolerance is a universally very frequent phenomenon and results in a more or less severe digestive disorder from milk and dairy products in the afflicted persons. Lactose intolerance is generally based on the absence of the enzyme lactase for whose formation a gene on chromosome 2 is responsible. This gene determines the time from which humans no longer produce lactase. Depending on the ethnic origin, this can be the case sooner or later. In earlier times of evolution, humans, like many other mammals, lost the enzyme always when they were no longer fed with breast milk (cf. Pharm. Ztg. No. 9, 145th annual volume, Mar. 2, 2000). Today, the $H_2$ breath test is employed most frequently for diagnosing lactose intolerance since it is simple and telling. Thus, the patient drinks a solution of 50 g lactose in water. The hydrogen subsequently exhaled is then measured repeatedly by gas chromatography over 4 hours. Thus, not only qualitative, but also quantitative information about the lactase deficiency is obtained.

Lactose intolerance is now considered a disease which can be treated only symptomatically to date. However, in the meantime, there has been found a possibility of ingesting the enzyme lactase in the form of capsules, tablets or solution and thus compensating the lactase deficiency.

In addition to the hydrogen in the breathing air as already mentioned, there is also a lactose tolerance test in which 50 g of lactose in water is administered to subjects on empty stomachs, followed by measuring the blood glucose level in such subjects over several hours. Unless the lactose is completely cleaved enzymatically, the glucose level remains low and thus confirms the lactose intolerance.

The diagnostic methods known to date have the drawback that a relatively high amount of lactose must be delivered to the patients, which may already lead to considerable complaints in many patients who suffer from lactose intolerance.

The assaying of the blood glucose level has the further drawback that the blood glucose level may be changed by secondary factors, for example, increased release of adrenalin due to stress.

Both prior art methods have the further disadvantage that the measurements must be performed with several samples over an extended period of time, which is inconvenient and stressing for the patient and adds to the costs.

In theory, it would be possible to perform the test with $^{13}C$-labeled lactose. However, one gram of $^{13}C$-labeled lactose costs U.S. $2,000. For the lactose breath test, at least 150 mg of 99% $^{13}C$-labeled lactose is needed.

It was the object of the invention to provide a better, less expensive and more precise method for diagnosing lactose intolerance which does not have the above disadvantages.

According to the invention, this object is achieved by the oral administration of defined amounts of lactose, followed by assaying metabolites of lactose, wherein the lactose administered contains 99% $^{13}C$-labeled lactose, i.e., in amounts of from 5 to 30 mg. After the administration of the $^{13}C$-lactose, the content of $^{13}C$-labeled glucose is determined in a blood sample taken at a defined time after the administration. Preferably, the $^{13}C$-lactose is administered in the form of a gelatin capsule. Thus, it is possible that the $^{13}C$-lactose reaches the small intestine without being absorbed in the stomach (enteric dosage form).

In addition, the method can be improved in expressiveness by additionally determining the content of $^{13}C$-labeled lactose and/or $^{13}C$-labeled lactic acid in a In addition, the method can be improved in expressiveness by additionally determining the content of $^{13}C$-labeled lactose and/or $^{13}C$-labeled lactic acid in a stool specimen obtained some time after the time of the blood sampling. This additional determination is necessary only if the examination of the serum sample for glucose does not show a significant increase of $^{13}C$ and thus the lactose intolerance has actually been established already.

Patients with a very pronounced lactose intolerance can be caused to suffer from diarrhoea by a reduced amount of as low as 5 to 10 g of lactose. In this case, such stool specimens still contain almost the entire amount of $^{13}C$-labeled lactose. In patients with a less pronounced lactose intolerance, it is possible for the enteric bacteria to metabolize the administered lactose wholly or partially into $^{13}C$-labeled lactic acid. In addition, in such cases, $^{13}C$-labeled methane and $H_2$ may also be formed; these are substantially more difficult to examine, however. A decrease of the pH values of the stool specimens from lactic acid is another indication of lactose intolerance. However, the pH value of the stool may be influenced by many other factors, so that this parameter is hardly suitable for diagnosing lactose intolerance with certainty.

In contrast to the previously employed diagnostic methods, the method according to the invention requires a significantly smaller amount of lactose, namely from 5 to 30 mg of $^{13}C$-lactose in one capsule. In patients with a severe lactose intolerance, this smaller amount does not lead to any complaints while the diagnostic method is performed.

However, it is of critical importance that the method according to the invention is essentially more precise and, in addition, more telling because it is not interfered with by secondary influences. This is true of the $H_2$ breath test, and to a much larger extent of the determination of glucose in the serum.

The determination of the $^{13}C$ content in the serum samples and/or stool specimens according to the invention is effected, in particular, by means of modern mass spectrography with previously performed gas chromatography or elemental analysis. In the meantime, these methods have been further developed and automated to such an extent that it is economically possible to send the samples from the patients to a central laboratory which has the appropriate equipment and have them examined there.

The central laboratory should analyze only the serum samples in the first place. If stool specimens are also sent in, these should be examined only if the corresponding serum sample did not exhibit a significant rise of the $^{13}C$-labeled glucose. When the $^{13}C$-content rises normally as compared with standard samples of a known $^{13}C$ content, it is already indicated that lactose is well tolerated and sufficiently decomposed into glucose by lactase. Only if there is no rise of the $^{13}C$ content, or a significantly lesser one, it can be established by examining the stool specimen whether the lactose intolerance is very severe or moderate.

If the test yields a normal increase of the $^{13}C$ content and yet milk and dairy products are poorly tolerated, this is due to other diseases than the wide-spread lactose intolerance. Thus, the method according to the invention may also be employed for differential diagnostics. Such a group of patients cannot be helped by make them ingest lactase preparations.

The method according to the invention is further illustrated by the following Example.

EXAMPLE

Before the beginning of the test, 0.3 to 0.5 ml of capillary blood is withdrawn from the subject's finger or earlobe on an empty stomach. Then, the subject ingests a gelatin capsule with 5 to 30 mg of $^{13}$C-labeled lactose. After 30 to 60 min from the ingestion of the labeled lactose, from 0.3 to 0.5 ml of blood is again withdrawn as described above. Serum is obtained from the blood samples by centrifugation. By means of a filter, higher molecular weight components (e.g., lipids and proteins) are removed from the serum samples. The filtrates are combusted for an elemental analysis. The $CO_2$, which is formed thereby from glucose, inter alia, is passed into an isotope mass spectrometer by which the $^{13}$C content is determined. As described above, both blood samples are evaluated. If a difference value $\Delta\delta$ of less than 1‰ is detected between the blood samples taken before and after the ingestion of $^{13}$C-lactose, there is lactose intolerance.

The test is performed according to the following scheme:

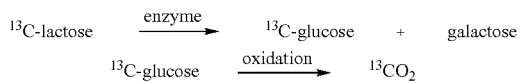

The patient takes a sample from his next stool and puts it into a sample container with a spatula. The next defecation is generally performed from 2 to 4 hours after the ingestion of the capsule. From the stool specimens, an aqueous extract is prepared in the laboratory and examined for $^{13}$C-lactose and/or $^{13}$C-lactic acid. The presence of $^{13}$C-lactose or $^{13}$C-lactic acid confirms the presence of a lactose intolerance.

The invention claimed is:

1. A method for diagnosing lactose intolerance in patients by the oral administration of defined amounts of lactose, followed by assaying metabolites of lactose, characterized in that the lactose administered contains 99% $^{13}$C-labeled lactose, and after the administration of the $^{13}$C-lactose, the content of $^{13}$C-labeled glucose is determined in a serum sample taken at a defined time after the administration, the amount of 99% $^{13}$C-lactose administered being from 5 to 30 mg.

2. The method according to claim 1, characterized in that said $^{13}$C-labeled lactose is administered in a capsule.

3. The method according to claim 1, characterized in that the content of $^{13}$C-labeled lactose and/or $^{13}$C-labeled lactic acid is additionally determined in a stool specimen obtained some time after the time of the serum sampling.

4. The method according to claim 1, characterized in that the serum sample is withdrawn about one hour after the administration of the lactose.

5. The method according to claim 3, characterized in that said stool specimen is taken 2 to 4 hours after the ingestion of the capsule.

6. The method according to claim 1, characterized in that the samples are sent to a central laboratory where they are examined for their $^{13}$C content by mass spectrography with previously performed gas chromatography.

7. A method according to claim 1, utilizing a kit comprising:
　1) from 5 to 30 mg of 99% $^{13}$C-labeled lactose in a capsule;
　2) a patient instruction manual;
　3) a blood sampling device;
　4) a sample container for collecting the blood sample; and optionally,
　5) a sample container and spatula for a stool specimen.

* * * * *